United States Patent [19]

Wittenberg

[11] 4,381,285

[45] Apr. 26, 1983

[54] CONTACT LENS STERILIZING DEVICE

[76] Inventor: Sidney Wittenberg, 52 Surrey La., Sudbury, Mass. 01776

[21] Appl. No.: 223,755

[22] Filed: Jan. 9, 1981

[51] Int. Cl.³ .............................................. A61L 2/18
[52] U.S. Cl. .................................. 422/116; 134/58 R; 134/78; 134/159; 134/160; 422/300
[58] Field of Search ...................... 422/116, 300, 301; 134/78, 113, 58 R, 138, 153, 156, 159, 160

[56] References Cited

U.S. PATENT DOCUMENTS

| | | | |
|---|---|---|---|
| 2,535,111 | 12/1950 | Wishaut | 134/160 |
| 2,556,495 | 6/1951 | Freedman | 422/300 |
| 2,692,603 | 10/1954 | Foote | 134/160 |
| 3,419,346 | 12/1968 | Nicholas | 422/300 |
| 3,837,805 | 9/1974 | Boucher | 422/301 |
| 4,013,410 | 3/1977 | Thomas et al. | 422/300 |
| 4,143,116 | 3/1979 | Meltzer | 422/116 |

*Primary Examiner*—Barry S. Richman

*Attorney, Agent, or Firm*—Sixbey, Friedman & Leedom

[57] ABSTRACT

The present invention comprises a contact lens sterilizing device (10,54,118) which chemically disinfects contact lenses (L) in a cell (20,64,134) containing antimicrobial solution (42,104,144) and which subsequently transfers the lenses (L) to a storage cell (22,66,136) containing storage solution (44,106,146). Momentum generated as the striker arm (6) of a mechanical timer (2) snaps from a first position to a second position is utilized to propel a cage (C,70,140) holding the contact lenses (L) from the sterilizing cell (20,64,134) to the storage cell (22,66,136), thereby effecting the transfer operation. In one embodiment (10) of the present invention, the striker arm momentum is indirectly imparted to the contact lens cage (C) via a flipper (28). In other embodiments (54,118) of the present invention, the striker arm momentum is directly imparted to the contact lens cage (70,140) via a hook (72,142) integrally formed on the cage (70,140).

18 Claims, 12 Drawing Figures

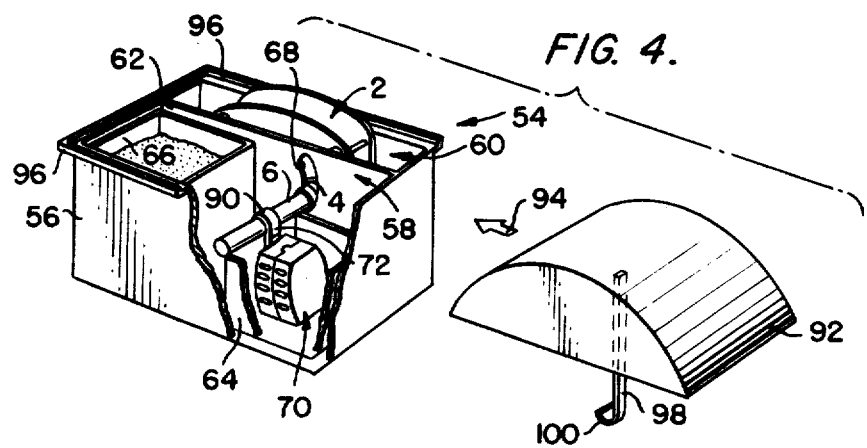
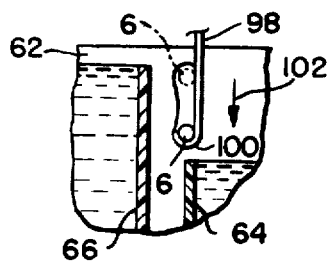
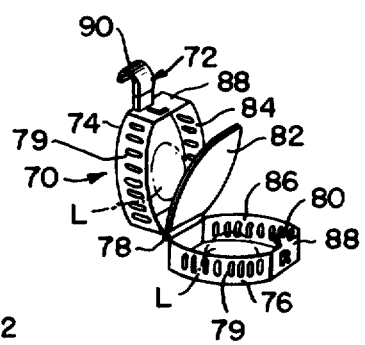
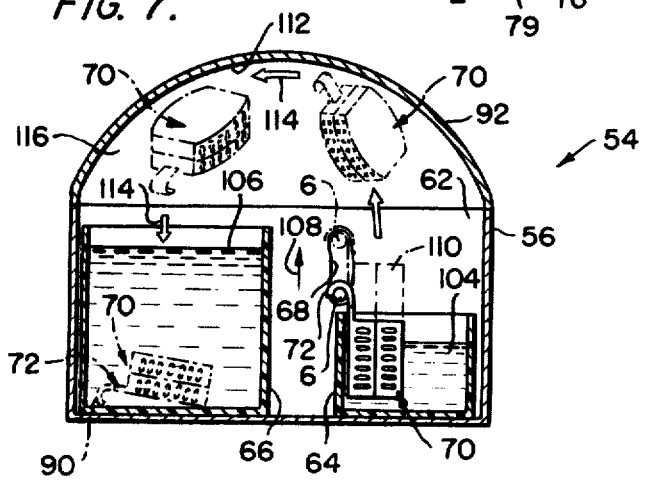

CONTACT LENS STERILIZING DEVICE

TECHNICAL FIELD

The present invention relates to a contact lens sterilizing device and more particularly to a device which submerges contact lenses in a disinfecting or sterilizing solution for a predetermined period of time and which subsequently transfers the contact lenses to a soaking solution at the completion of the sterilizing process in order to properly store the lenses until they are worn again.

BACKGROUND ART

The advent of soft contact lenses fabricated from pliable plastic materials has greatly increased the comfort and convenience associated with wearing contact lenses. Unlike the earlier "hard" contact lenses, however, soft contact lenses are generally quite hydrophilic and are thus susceptible to contamination by micro-organisms. Accordingly, soft contact lenses must be disinfected or sterilized daily if irritation or infection of the wearer's eyes is to be avoided.

Many of the contact lens sterilizing techniques heretofore developed rely upon the heating of the lenses to a high temperature in the presence of a saline solution, whereby destruction of the micro-organisms is achieved. Of course, before heat sterilized lenses can be safely reinserted in a wearer's eyes, the lenses must cool sufficiently. Numerous means have been devised, both in the contact lens sterilizing field per se and in analgous arts, for decreasing the amount of time necessary to complete this cooling step. U.S. Pat. No. 2,556,495, for instance, issued to Freedman on June 12, 1951, discloses a sterilizing apparatus wherein articles supported in a sterilizing tray are removed from the hot water of a sterilizing tank through the actuation of a link and lever mechanism and deposited in a receptacle containing cooling fluid. Despite the efforts by Freedman and others to reduce the inconvenience associated therewith, the use of heat to achieve sterilizing action requires relatively bulky and complicated equipment, thus rendering heat sterilization processes cumbersome with respect to small articles in general and contact lenses in particular.

Several contact lens sterilizing techniques overcome the disadvantages inherent in heat sterilizing systems by employing anti-microbial solutions in lieu of heat to carry out the sterilizing operation. U.S. Pat. No. 3,912,451, issued Oct. 14, 1975, describes such a technique for sterilizing contact lenses with hydrogen peroxide ($H_2O_2$). Unfortunately, the use of anti-microbial solutions is not without its own drawbacks, inasmuch as many anti-microbial solutions are injurious to the eyes. Care must consequently be taken to insure that any sterilizing solution remaining on the contact lenses after chemical treatment has been completed is neutralized before the lenses are worn again. Examples of apparatus for controlling both the immersion of contact lenses in an anti-microbial solution of hydrogen peroxide and the neutralization of the solution following sterilization can be found in U.S. Pat. No. 4,013,410, issued to Thomas et al on Mar. 22, 1977 and U.S. Pat. No. 4,143,116, issued to Meltzer on Mar. 6, 1979. Thomas et al specifically discloses a timer actuated rotatable bracket which automatically flips a capsule containing contact lenses submerged in hydrogen peroxide from an upright position to an inverted position after a predetermined interval of time, whereupon the hydrogen peroxide flows into contact with a catalytic agent and is reduced to water. Meltzer also relies upon the inversion of a contact lens-carrying capsule to bring the lens sterilizing solution into contact with a neutralizing substance, but instead of the rotatable bracket of Thomas et al, Meltzer utilizes a cammed catch release arrangement to permit gravity assisted swinging of the capsule into the inverted position.

It can be seen that the aforementioned patents teach a practical means for chemically destroying potentially injurious micro-organisms on contact lenses. Nevertheless, the Meltzer and Thomas et al apparatus exhibit certain inherent limitations. Neither Meltzer nor Thomas et al actually remove the contact lenses from the hydrogen peroxide subsequent to the sterilizing process. Hence, the entire volume of hydrogen peroxide used in the Meltzer and Thomas et al apparatuses must be neutralized in order to render the contact lenses wearable. Neutralization of such a relatively large amount of hydrogen peroxide in turn consumes a disproportionate amount of time. Moreover, the hydrogen peroxide once neutralized provides a less than ideal storage environment for the lenses. As a net result, the prior art fails to disclose a truly simple, reliable, yet effective device for chemically sterilizing contact lenses in a relatively short period of time with a minimum of risk to the contact lens wearer.

DISCLOSURE OF INVENTION

It is therefore a primary object of the present invention to provide a means for subjecting contact lenses to the anti-microbial action of a sterilizing solution and for storing the lenses in a optimum storage environment subsequent to the sterilizing process.

It is an additional object of the present invention to provide a means for submerging contact lenses in an anti-microbial sterilizing solution during a first interval of time and for transferring the contact lenses to a storage or soaking solution upon completion of the first interval of time, which soaking solution also acts to neutralize any sterilizing solution remaining on the contact lenses following the transfer operation.

It is yet an additional object of the present invention to provide a means for utilizing a simple mechanical action to transfer contact lenses from a sterilizing solution to a storage solution upon completion of a first predetermined interval of time.

It is a further object of the present invention to provide a contact lens sterilizing means wherein the short, essentially linear motion of a mechanical striker is converted into a longer, curvilinear translatory motion suitable for propelling contact lenses from a sterilizing cell to a storage cell.

It is also an object of the present invention to provide a contact lens sterilizing means having a curved guide surface for accurately guiding contact lenses along a curvilinear path from a sterilizing cell toward a storage cell.

These and other objects of the present invention are achieved by a contact lens sterilizing device which includes a support case divided into a lens sterilization and storage compartment and a timer compartment. Two cells respectively containing anti-microbial solution and storage solution are arranged in side-by-side relationship within the lens sterilization and storage compartment. A mechanical timer having a striker arm which projects into the lens sterilization and storage compartment is secured within the timer compartment. The striker arm of the timer is designed to snap across a short arc at the end of a predetermined time interval. In a first embodiment of the present invention, the timer is oriented such that the striker arm moves in a vertical direction relative to the sterilizing and storage cells. A free swinging flipper is pivotally mounted in the sterilization and storage compatment and rests across the striker arm. At the outset of the sterilizing process, a contact lens cage containing the contact lenses to be sterilized is placed on the platform of the flipper. The striker arm is set in a loaded position, whereupon the platform drops into the sterilizing cell and the contact lens cage supported thereon is submerged in sterilizing solution. When the predetermined interval of time expires, the striker arm is actuated by the mechanical timer to swing the flipper out of the sterilizing cell, thus propelling the contact lens cage from the sterilizing cell along a curvilinear path to the storage cell. After the contact lenses have soaked in the storage solution for a second interval of time, all traces of sterilizing solution are removed from the lenses and the lenses may be worn again without fear of injury to the wearer's eyes.

In a second embodiment of the present invention, the striker arm of the mechanical timer is also disposed within the lens sterilization and storage compartment for vertical movement. The flipper of the first embodiment, however, is removed from the lens sterilization and storage compartment and a hook is attached to the contact lens cage itself. The hook is subsequently placed over the striker arm and the contact lens cage is immersed in the sterilizing solution. The snap action of the striker arm at the expiration of the first predetermined time interval imparts momentum directly to the contact lens cage, again propelling the cage from the sterilizing cell to the storage cell. A lid structure having a curved surface is provided to align the trajectory of the cage.

A third embodiment of the present invention employs a mechanical timer oriented to provide horizontal striker arm movement. The hooked contact lens cage of the second embodiment is draped over the striker arm and immersed in the sterilizing solution. The actuation of the striker arm at the end of the sterilizing process pulls the contact lens cage across the edge of the sterilizing cell, which edge acts as a fulcrum to rotate the cage through a 90° turn. Continued movement of the striker arm imparts a significant horizontal component of momentum to the cage, and the cage is propelled along an essentially horizontal path until dropping into the storage cell.

The various features and advantages of the present invention will become even more apparent from the following Brief Description of the Drawings and Best Mode For Carrying Out the Invention.

BRIEF DESCRIPTION OF THE DRAWINGS

FIG. 4 is a perspective cut-away illustrating a second embodiment of a contact lens sterilizing device constructed in accordance with the present invention, wherein the momentum of the striker arm is imparted directly to the contact lens cage.

FIG. 5 is a perspective view of a contact lens cage suitable for use with the device of FIG. 4.

FIG. 6 is a partial cross-sectional view of the top locking arm used in conjunction with the FIG. 4 embodiment.

FIG. 7 is a cross-sectional view illustrating the operation of the FIG. 4 embodiment in detail.

BEST MODE FOR CARRYING OUT THE INVENTION

Figure 1A:
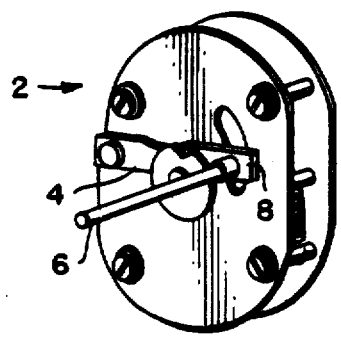
FIG. 1A is a perspective view of a mechanical timer suitable for use with the contact lens sterilizing device of the present invention.
Figure 1B:
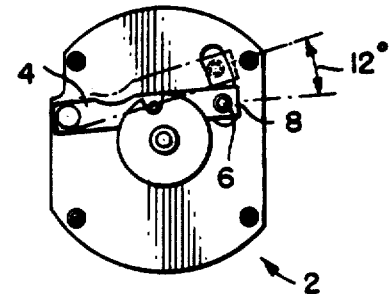
FIG. 1B is a front view of the mechanical timer of FIG. 1A, showing in particular the motion of the timer trip lever and striker arm.

The contact lens sterilizing device of the present invention utilizes a simple linear mecanical motion to transfer contact lenses from a sterilizing solution to a storage solution. This motion is supplied by a mechanical timer 2 as depicted in FIGS. 1A and 1B. In preferred form, timer 2 may comprise a MARK-TIME 1900 series spring-driven movement (available from M. H. Rhodes, Inc. of Avon, Conn.), and thus requires no batteries or other electrical power source. The 1900 series timer includes a trip lever 4 which, at the end of a predetermined time interval, automatically snaps from a loaded position (indicated by solid lines in FIG. 1B) to an unloaded position (indicated by phantom lines in FIG. 1B) with an 8 ounce force. The motion of trip lever 4 is transmitted to a striker arm 6 secured to one end 8 of the trip lever. As seen to best advantage in FIG. 1B, this motion is essentially linear with respect to striker arm 6. The predetermined time interval can range from 6 seconds to 12 hours, and is set by adjusting a timer dial (not shown in FIGS. 1A and 1B) to the desired value.

Figure 2:
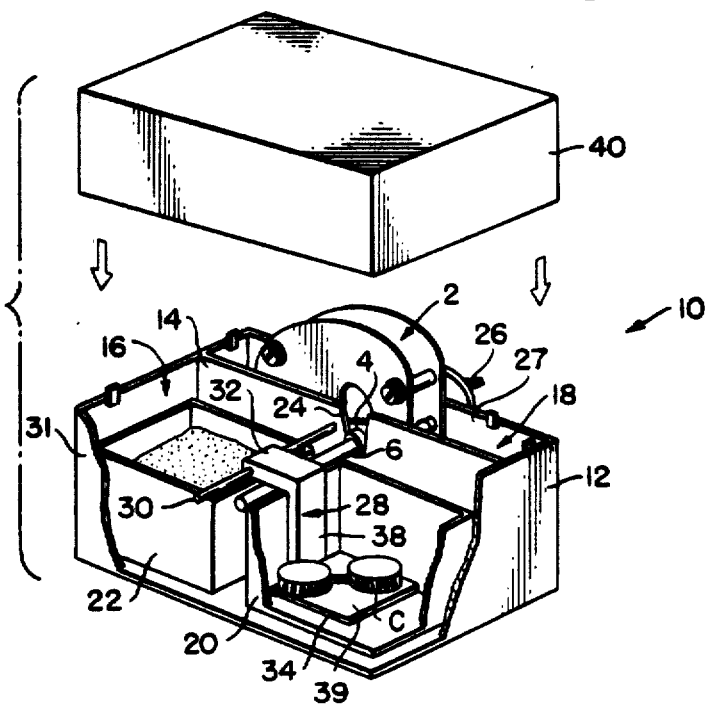
FIG. 2 is a perspective cut-away illustrating a first embodiment of the present invention, wherein a flipper disposed in a cell containing anti-microbial sterilizing solution is adapted to propel contact lenses from the sterilizing solution toward a cell containing storage solution in response to actuation of the mechanical timer shown in FIGS. 1A-B.

FIG. 2 illustrates one embodiment of a contact lens sterilizing device 10 constructed in accordance with the present invention. Sterilizing device 10 includes a support case 12 manufactured from metal, plastic or other suitably durable material. A partitioning wall 14 divides support case 12 into a lens sterilization and neutralization compartment 16 and a timer compartment 18. A sterilizing vat or cell 20 for holding an anti-microbial solution (i.e., a sterilizing or disinfecting solution) and a storage cell 22 for holding a storage solution are disposed in side-by-side relationship within lens sterilization and storage compartment 16. Sterilizing cell 20 and storage cell 22 may be manufactured from plastic or metal in a configuration which permits easy removal of the cells from the lens sterilization and storage compartment. Each cell could, for example, be designed with the box-like configuration depicted in FIG. 2. Support case 12 would then have suitable holding means (not shown) for retaining sterilizing and storage cells 20,22 in lens sterilization and storage compartment 16. Alternately, cells 20 and 22 could be arranged in a drawer-like manner (not shown) to slide in and out of the lens sterilization and storage compartment. The mechanical timer 2 of FIGS. 1A and 1B is secured within timer compartment 18. Striker arm 6 of timer 2 projects into lens sterilization and storage compartment 16 through a slot 24 formed in partitioning wall 14, while the timer dial 26 used in setting the predetermined time interval projects from the back wall 27 of support case 12. Timer 2 is oriented such that striker arm 6 moves in essentially vertical fashion as trip lever 4 snaps from the loaded position depicted in FIG. 2 to the unloaded position described in connection with FIG. 1B. A free-swinging flipper 28 is pivotally mounted on a shaft 30 extending between partitioning wall 14 and front wall 31 of support case 12. Flipper 28 includes a pivot arm 32 which rests against striker arm 6, a platform 34 which supports a contact lens cage C, and an intermediate arm 38 which interconnects pivot arm 32 and platform 34. The primary purpose of contact lens cage C is to maintain the left and right contact lenses in separate, readily identifiable locations throughout the operation of sterilizing device 10. To this end, any commercially available contact lens cage having apertures which permit fluid to flow into contact with the lenses may be employed with the FIG. 2 embodiment of the present invention. Platform 34 may consist of either a solid construction having a lens cage supporting surface 39, as depicted in FIG. 2, or an open wire frame structure suitable for holding contact lens cage C. A lid structure 40 fits over support case 12 to protect the various components of the sterilizing device during the sterilization and neutralization processes and to contain contact lens cage C during transfer from the sterilizing to the storage cells. If desired, lid structure 40 may be fabricated from a clear plastic material in order to admit light into the interior of lens sterilization and storage compartment 16. This feature is important where a light-activated disinfecting solution such as an iodine-based disinfectant is used to fill the sterilizing cell.

Figure 3:
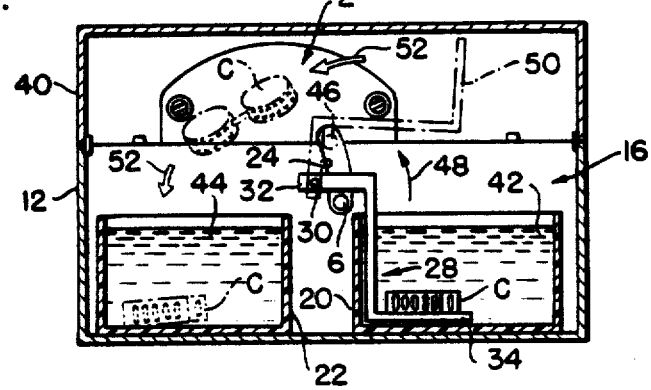
FIG. 3 is a cross-sectional view depicting the operation of the device illustrated in FIG. 2.

The operation of contact lens sterilizing device 10 is graphically illustrated in FIG. 3. Sterilizing cell 20 is initially filled with an anti-microbial solution 42, while storage cell 22 is filled with a soaking solution 44. In addition to providing a storage environment for the contact lenses, storage solution 44 must act to neutralize any sterilizing solution remaining on the contact lenses after the lenses have been transferred to the storage cell. SEPTICON TM soaking solution is one well known type of fluid which performs both the storage and neutralizing functions. A pair of contact lenses to be sterilized is placed in the contact lens cage C and the contact lens cage is placed on platform 34 of flipper 28. Of course, contact lens cage C could be dispensed with entirely if desired and the contact lenses placed directly on platform 34 to provide a simpler operating mode for device 10. Dial 26 is next set to provide the desired time interval for the sterilizing process, resulting in the cocking of trip lever 4 and the corresponding movement of striker arm 6 to the loaded position indicated in solid lines in FIG. 3. Pivot arm 32 continues to rest against striker arm 6, causing platform 34 of flapper 28 to drop into sterilizing cell 20. The contact lenses contained in contact lens cage C are thus submerged in antimicrobial solution 42 and subjected to a sterilizing action. Lid structure 40 may be fastened over support case 12 to complete the manual phase of the operation. At the end of the timer interval determined by the setting of dial 26, timer trip lever 4 automatically snaps across the arc discussed in connection with FIG. 1B and striker arm 6 moves to the position outlined in phantom at 46 in FIG. 3. The movement of striker arm 6 simultaneously rotates pivot arm 32 about shaft 30 in the direction of arrow 48. Platform 34 is accordingly displaced through an angle of approximately 90° and assumes the position outlined in phantom at 50 in FIG. 3. Momentum imparted to the contact lens cage C by the displacement of platform 34 propels the contact lens cage toward storage cell 22 along a curvilinear path as indicated by arrows 52. The lens cage thereafter drops into the storage cell and storage solution 44 flows onto the contact lenses to remove or neutralize any sterilizing solution remaining on the lenses.

An alternative embodiment of a contact lens sterilizing device is shown in FIGS. 4–6. The sterilizing device, generally designated at 54, is similar in many respects to the sterilizing device 10 of FIG. 2. Sterilizing device 54 includes a support case 56 which is divided into a lens sterilization and storage compartment 58 and a timing compartment 60 by a partitioning wall 62. A sterilizing cell 64 and a storage cell 66 are again placed side-by-side in lens neutralizing and storage compartment 58. For reasons described in detail hereinbelow, the volume of storage cell 66 is greater than that of sterilizing cell 64. Mechanical timer 2 is secured inside timing compartment 60 with striker arm 6 projecting into lens sterilization and storage compartment 58. As was the case with the FIG. 2 embodiment of the present invention, the striker arm moves in essentially vertical fashion in response to the snap action of timer trip lever 4. A slot 68 formed in partitioning wall 62 accomodates this striker arm movement. Unlike the FIG. 2 embodiment, however, sterilizing device 54 has no free-swinging flipper assembly mounted in lens sterilization and storage compartment 58. Rather, sterilizing device 54 employs a contact lens cage 70 which directly engages striker arm 6 via a hook-like element 72. The need to provide clearance for the rotation of the FIG. 2 flipper assembly is thus eliminated, and a concomitant reduction in the overall size of sterilizing device 54 is achieved.

Contact lens cage 70 is shown in detail in FIG. 5. Contact lens cage 70 includes a first cage portion 74 and a second cage portion 76 joined at hinge 78 to permit opening and closing of the first and second cage portions relative to one another. Apertures 79 formed along the sides of first and second portions 74, 76 permit the free flow of fluid therethrough. A snap 80 or other fastener located at the end of second cage portion 76 opposite hinge 78 may be used to secure the first and second cage portions in the closed position. A thin, semi-rigid partition 82 attached to hinge 78 serves to divide the interior of contact lens cage 70 into left and right lens accomodating areas, respectively designated 84 and 86. In this manner, the left and right members of a pair of contact lenses L can be separated during the sterilizing process to assist the wearer in identifying the lenses prior to reinserting them in his or her eyes. Appropriate indicia 88 can be formed on each of the cage portions. As previously mentioned, contact lens cage 70 also includes a hook 72 for engaging the mechanical timer striker arm. Hook 72 is integrally joined to first cage portion 74. A segment 90 of the hook may be formed from a catalytic agent such as platinum; as described in greater detail hereinbelow, such a construction minimizes the danger that injury will result from inadvertantly filling the storage cell of sterilizing device 54 with sterilizing solution.

Returning briefly to FIG. 4, it can be seen that support case 56 of sterilizing device 54 is covered with a curved lid structure 92. Lid structure 92 is designed to slide onto support case 56, as indicated by arrow 94, and to this end the front and back walls of support case 56 are constructed with simple track assemblies 96 for receiving lid structure 92. If desired, a lid locking arm 98 can be formed on lid structure 92 to provide a means for clamping the lid structure securely in place on support case 56 while the sterilizing process is carried out. Lid structure 92 may also contain a partitioning wall (not shown in FIG. 4) to prevent contact lens cage 70 from accidentially falling into timing compartment 60 during the transfer of the contact lens cage from the sterilizing cell to the storage cell.

FIG. 6 furnishes a detailed view of the manner in which lid locking arm 98 functions to secure lid structure 92 to the top of support case 56. Lid structure 92 is placed on the support case track assemblies 96 prior to the setting of mechanical timer 2. Consequently, trip lever 4 is in the unloaded position and striker arm 6, as outlined in phantom in FIG. 6, remains above the hook end 100 of lid locking arm 98. When lid structure 92 is properly aligned on support case 56, the lid locking arm abuts striker arm 6. Thereafter, the cocking of timer trip lever 4 moves striker arm 6 in the direction indicated by arrow 102 to the solid line position outlined in FIG. 6. In this position, the striker arm firmly engages the hook end 102 of lid locking arm 98 to secure lid structure 92 in place on top of support case 56.

The operation of contact lens sterilizing device 54 is illustrated in FIG. 7. Sterilizing cell 64 and storage cell 66 are respectively filled with an anti-microbial solution 104 and a storage solution 106. The hook 72 of contact lens cage 70 is draped over striker arm 6, lid 92 is placed on support case 56 and the timer knob (not shown in FIGS. 4–7) is set at the desired time interval, whereupon striker arm 6 moves to the loaded or solid line position in FIG. 7. Loading of the striker arm 6 in turn causes contact lens cage 70 to drop into sterilizing cell 64, and the contact lenses contained in cage 70 are immersed in the anti-microbial solution 104. As previously explained in connection with FIG. 6, the loading of striker arm 6 may also provide a clamping force to secure lid structure 92 on support case 56. At the end of the time interval determined by the setting of the timer knob, the snap action of the timer trip lever, detailed in connection with FIG. 1B, moves striker arm 6 in the direction of arrow 108 to the position outlined in phantom in FIG. 7. The momentum acquired by striker arm 6 is transferred directly to contact lens cage 70 via hook 72. This momentum is sufficient to lift cage 70 from sterilizing cell 64 to the position outlined in phantom at 110 in FIG. 7 and to subsequently propel the contact lens cage upward toward lid structure 92. The curved inner surface 112 of the lid structure guides the trajectory of contact lens cage 70 along the curvilinear path indicated by arrows 114, and the contact lens cage ultimately drops into storage cell 66 where soaking solution 106 removes any harmful traces of sterilizing solution remaining on the contact lenses. The aforementioned partitioning wall 116 formed on the inside of lid structure acts as a barrier to prevent contact lens cage 70 from accidentially falling into the timing compartment of sterilizing device 54. The increased volume of storage cell 66 relative to sterilizing cell 64 serves to prevent storage solution 106 from splashing around the interior of lens sterilization and storage compartment 58 when the contact lens cage drops into storage cell 66.

It is instructive to recall that the hook 72 of contact lens cage 70 may include a section 90 fabricated from a catalytic agent such as platinum. The purpose behind this construction can be discerned upon closer examination of FIG. 7. If the contact lens wearer inadvertantly or mistakenly fills storage cell 66 with a sterilizing solution rather than a storage solution, the catalytic agent 90 on hook 72 will chemically reduce the sterilizing solution to a harmless fluid after contact lens cage 70 falls into storage cell 66. The present invention accordingly provides a means for minimizing the risk of accidential injury to the contact lens wearer's eyes.

Figure 8:
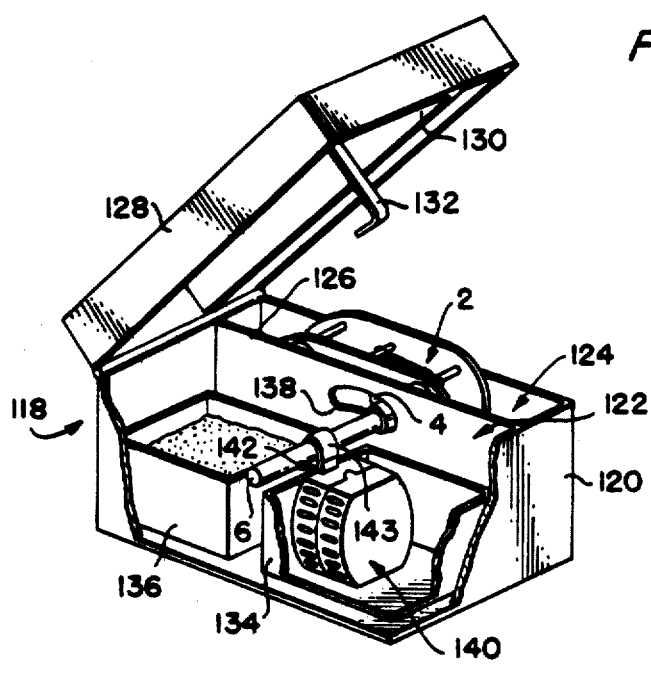
FIG. 8 is a perspective cut-away showing a third embodiment of a contact lens sterilizing device constructed in accordance with the present invention, wherein the trip lever and striker arm of the mechanical timer are diposed for horizontal movement.
Figure 9:
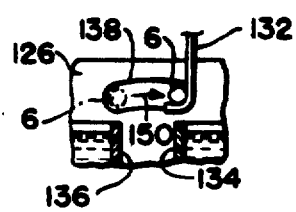
FIG. 9 is a partial cross-sectional view of the top locking arm used in conjunction with the FIG. 9 embodiment.
Figure 10:
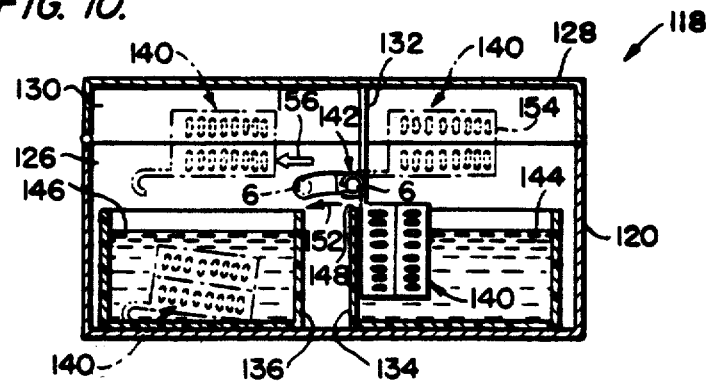
FIG. 10 is a cross-sectional view illustrating the operation of the FIG. 8 embodiment in detail.

Yet a third embodiment of the present invention is illustrated in FIGS. 8–10. Contact lens sterilizing device 118 comprises a support case 120 divided into lens sterilization and storage compartment 122 and timing compartment 124 by partitioning wall 126. A lid structure 128 containing a partitioning wall 130 and a lid locking arm 132 is hinged to one end of support case 120. Sterilizing cell 134 and storage cell 136 are placed in lens sterilization and storage compartment 122. A mechanical timer 2 with a projecting striker arm 6 is secured in timing compartment 124, but in contrast to the FIG. 2 and FIG. 4 embodiments the striker arm 6 of sterilizing device 118 is arranged to move along an essentially horizontal path in lens sterilization and storage compartment 122. Slot 138 in partitioning wall 126 is accordingly formed with an essentially horizontal orientation. A contact lens cage 140 of the type disclosed in FIG. 5 is draped over striker arm 6 with the hook 142 of the contact lens cage resting directly upon the striker arm. If desired, hook 142 may contain a section 143 fabricated from a catalytic agent such as platinum in order to protect the contact lens wearer against accidental filling of storage cell 136 with sterilizing solution.

The operation of sterilizing device 118 is illustrated in FIGS. 9 and 10. Sterilizing cell 134 is again filled with an anti-microbial solution 144 or the like, the storage cell 136 is filled with a neutralizing soaking or storage solution 146. Contact lens cage 140 is hooked over striker arm 6 and lid 128 is closed. Mechanical timer 2 is then set by adjusting the timer dial (not shown in FIGS. 8–10), which adjustment loads trip lever 4 and causes striker arm 6 to assume the solid line position of FIGS. 9 and 10. Referring specifically to FIG. 10, it can be seen that contact lens cage 140 slides across the edge 148 of sterilizing cell 134 and into solution 144 as trip lever 4 is cocked. Referring specifically to FIG. 9, it can also be seen that the cocking of trip lever 4 moves striker arm 6 into engagement with lid locking arm 132, as indicated by arrow 150, to secure lid structure 138 firmly in place on support case 120. The lenses in contact lens cage 140 continue to soak in solution 144 throughout the duration of the predetermined time interval set by the adjustment of the timer dial. Expiration of the predetermined time interval, of course, triggers trip lever 4 into snapping, at which point striker arm 6 moves in the direction of arrow 152 to the position outlined in phantom in FIG. 10. The initial movement of the striker arm pulls contact lens cage 140 sharply against edge 148 of the sterilizing cell 134. Edge 148 in turn acts as a fulcrum to swing the contact lens cage out of sterilizing cell 134 and into the roughly horizontal position outlined at 154. The remaining movement of striker arm 6 imparts a horizontal momentum to contact lens cage 140, propelling the contact lens cage along the horizontal path indicated by arrow 156. After a short distance, contact lens cage 140 drops into storage cell 136 where any sterilizing solution remaining on the contact lenses is neutralized. Partitioning wall 130 in lid structure 128 again serves to prevent the contact lens cage from accidentially falling into timing compartment 124.

Figure 11:
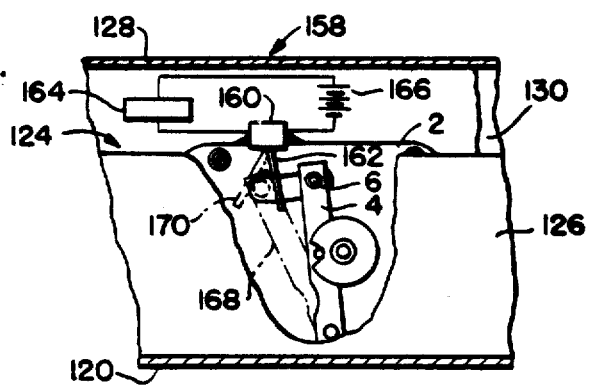
FIG. 11 is a cut-away view showing the installation of a storage timer in the contact lens sterilizing device of FIGS. 8-10.

A storage timer circuit for signalling the end of the neutralizing period (i.e., the end of an interval of time sufficient to insure neutralization of all sterilizing solution remaining on the contact lenses following transfer of the lenses from the sterilizing cell to the storage cell) would provide further advantages in practicing the present invention. FIG. 11 illustrates one embodiment of a storage timer circuit 158 as installed in the contact lens sterilizing device 118 of FIGS. 8-10. Storage timer circuit 158 includes a toggle-type switch 160 having a switch lever 162 normally biased to an open position, an electrical timer 164 with an alarm for indicating the passage of a predetermined interval of time, and an electrical power source 166. Switch 160 is secured to mechanical timer 2 such that switch lever 162 lies in the path of movement of striker arm 6. Electrical timer 164 and power source 166 are conveniently mounted within timing compartment 124 and are connected to one another through switch 160 to complete the construction of storage timer circuit 158.

When lid structure 128 is closed over support case 120 and mechanical timer 2 is loaded, trip lever 4 assumes the position outlined in solid lines in FIG. 11. Switch lever 162 is free to move to the open position, also outlined in solid lines in FIG. 11, and no current flows from power source 166 to electrical timer 164. When, however, trip lever 4 snaps to initiate the transfer of the contact lenses from sterilizing cell 134 (not shown in FIG. 11) to storage cell 136 (not shown in FIG. 11), as outlined in phantom at 168, striker arm 6 moves switch lever 162 to the closed position outlined in phantom at 170. Current then flows from power source 166 through switch 160 to activate electrical timer 164. Following a predetermined interval of time, sufficient to insure that all sterilizing solution remaining on the contact lenses is neutralized by the storage solution in the storage cell, the alarm of electrical timer 164 is energized to provide an indication that the contact lenses may be safely removed from sterilization device 118 and worn. The alarm may be audible, visual or both. If a visual alarm is employed, an indicator strip (not shown) could be placed on the outer surface of lid structure 128 to enable unrestricted viewing of the alarm.

As an alternative to the storage timer circuit 158 of FIG. 11, a mechanical storage timer (not shown) actuable by striker arm 6 could be mounted in the timing compartment to provide a signal at the end of the neutralizing period. If desired, a locking mechanism (not shown) designed to operate in conjunction with the storage timer could also be mounted in the timer compartment to prevent the lid structure from opening prior to the completion of the neutralizing process.

INDUSTRIAL APPLICABILITY

The present invention employs an anti-microbial solution in lieu of heat to achieve sterilizing action. The chemical nature of the sterilization process requires treatment of the sterilized objects with a storage and neutralizing agent after sterilization is complete. The devices of the present invention accordingly harness a simple linear mechanical motion to supply the momentum necessary for transfering articles from a sterilizing cell to a storage and neutralizing cell. Although the preferred mode of practicing the present invention is directed to a means for sterilizing contact lenses, it is clear that the underlying principles and concepts of the present invention are equally applicable to the construction of sterilizing devices for use with dental appliances, medical instruments, personal hygiene products and the like.

Only three embodiments of the present invention have been shown and described in the specification. It is nevertheless understood that various additional changes and modifications in the form and detail of the novel contact lens sterilizing devices illustrated above may be made by those skilled in the art without departing from the scope and spirit of the present invention. It is, therefore, the intention of the inventor to be limited only by the following claims.

I claim:

1. A device for sterilizing articles with a sterilizing solution and for subsequently transferring the articles to a storage environment after completion of the sterilization process, said device comprising:
   (a) a first receptacle containing sterilizing solution;
   (b) a second receptacle containing storage solution;
   (c) support means disposed in said first receptacle for holding the articles in fluid contact with the sterilizing solution;
   (d) momentum generating means movable between a first position and a second position to generate momentum; and
   (e) means for transmitting the momentum generated by said momentum generating means to said support means to impart motion to said support means and to forcefully drive the articles along a trajectory from said first receptacle to said second receptacle.

2. A device for sterilizing articles with a sterilizing solution and for subsequently transferring said articles to a storage environment at the completion of the sterilization process, said device comprising:
   (a) a first cell structure containing sterilizing solution;
   (b) a second cell structure containing storage solution;
   (c) a cage means disposed in said first cell structure for holding the articles in fluid contact with the sterilizing solution;
   (d) timer means for measuring a predetermined interval of time, said timer means including a striker arm which generates momentum by moving from a first position to a second position at the expiration of said predetermined interval of time; and
   (e) means for transmitting the momentum generated by said striker arm to said cage means to propel said cage means from said first cell structure to said second cell structure at the expiration of said predetermined interval of time.

3. A device for sterilizing contact lenses with a sterilizing solution and for subsequently transferring the contact lenses to a storage environment after completion of the sterilization process, said device comprising:
(a) a first cell structure containing sterilizing solution;
(b) a second cell structure containing storage solution;
(c) cage means disposed in said first cell structure for holding the contact lenses in fluid contact with the sterilizing solution;
(d) timer means for measuring a predetermined interval of time, said timer means including a striker arm which generates momentum by moving from a first position to a second position at the expiration of said predetermined interval of time; and
(e) means for transmitting the momentum generated by said striker arm to said cage means to propel said cage means from said first cell structure to said second cell structure at the expiration of said predetermined interval of time.

4. A device as set forth in claim 3, including a storage timer means for measuring an additional predetermined interval of time and for signalling the end of said additional predetermined interval of time, said storage timer means being mounted for activation in response to the movement of said striker arm from said first position to said second position.

5. A device as set forth in claim 3, wherein said means for transmitting said momentum includes a free-swinging flipper structure pivotally mounted relative to said first and second cell structures, said flipper structure having a pivot arm which rests across said striker arm and a platform which rests in said first cell structure when said striker arm is in said first position.

6. A device as set forth in claim 5, including a support case divided into at least first and second compartments, said first and second cell structures being arranged in side-by-side relationship within said first compartment and said timer means being arranged within said second compartment such that said striker arm projects into said first compartment.

7. A device as set forth in claim 3, wherein said means for transmitting said momentum includes a hook means attached to said cage means for hanging over said striker arm when said striker arm is in said first position.

8. A device as set forth in claim 7, wherein said hook structure includes at least one segment fabricated from a catalytic agent which is effective to neutralize said sterilizing solution when brought into contact with said sterilizing solution.

9. A device as set forth in claim 7, wherein said timer means is oriented relative to said first and second cell structures such that said striker arm moves from said first position to said second position in essentially vertical fashion relative to said first and second cell structures.

10. A device as set forth in claim 9, including a supporting case divided into at least first and second compartments, said first and second cell structures being arranged in side-by-side relationship within said first compartment and said timer means being arranged within said second compartment such that said striker arm projects into said first compartment.

11. A device as set forth in claim 10, including a lid structure which covers said supporting case to contain said cage means as said cage means is propelled from said first cell structure to said second cell structure.

12. A device as set forth in claim 11, wherein said lid structure has a curved surface which serves to accurately guide said cage means as said cage means is propelled from said first cell structure to said second cell structure.

13. A device as set forth in claim 11, wherein said lid structure includes a lid locking arm which is engaged by said striker arm when said striker arm is in said first position in order to secure said lid structure in place on said supporting case.

14. A device as set forth in claim 7, wherein said timer means is oriented relative to said first and second cell structures such that said striker arm moves from said first position to said second position in an essentially horizontal fashion relative to said first and second cell structures.

15. A device as set forth in claim 14, including a supporting case divided into at least first and second compartments, said first and second cell structures being arranged in side-by-side relationship within said first compartment and said timer means being arranged within said second compartment such that said striker arm projects into said first compartment.

16. A device as set forth in claim 15, including a lid structure which covers said supporting case to contain said cage means as said cage means is propelled from said first cell structure to said second cell structure.

17. A device as set forth in claim 16, wherein said lid structure includes a lid locking arm which is engaged by said striker arm when said striker arm is in said first position to secure said lid structure in place on said supporting case.

18. A device as set forth in claim 11 or 16, wherein said lid structure is formed from a transparent material.

* * * * *